US006379374B1

(12) United States Patent
Hieshima et al.

(10) Patent No.: US 6,379,374 B1
(45) Date of Patent: Apr. 30, 2002

(54) SMALL DIAMETER EMBOLIC COIL HYDRAULIC DEPLOYMENT SYSTEM

(75) Inventors: Grant Hieshima, Huntington Beach, CA (US); Robert Lulo, Pembroke Lakes, FL (US)

(73) Assignee: Cordis Neurovascular, Inc., Miami Lakes, FL (US)

(*) Notice: Subject to any disclaimer, the term of this patent is extended or adjusted under 35 U.S.C. 154(b) by 0 days.

(21) Appl. No.: 09/580,684

(22) Filed: May 30, 2000

Related U.S. Application Data

(63) Continuation-in-part of application No. 09/177,848, filed on Oct. 22, 1998, now Pat. No. 6,113,622.

(51) Int. Cl.7 .............................................. A61M 29/00
(52) U.S. Cl. ...................................... 606/200; 606/108
(58) Field of Search .............................. 606/200, 108, 606/198, 191, 194, 206, 205, 1; 623/1.11, 1.22

(56) References Cited

U.S. PATENT DOCUMENTS

| 2,853,070 A | 9/1958 | Julliard |
| 3,334,629 A | 8/1967 | Cohn |
| 3,353,718 A | 11/1967 | McLay |
| 4,512,338 A | 4/1985 | Balko et al. |
| 4,734,093 A | 3/1988 | Bonello et al. |
| 4,743,230 A | 5/1988 | Nordquest |
| 4,811,737 A | 3/1989 | Rydell |
| 4,832,692 A | 5/1989 | Box et al. |
| 4,906,241 A | 3/1990 | Noddin et al. |
| 4,919,121 A | 4/1990 | Rydell et al. |
| 4,938,220 A | 7/1990 | Mueller, Jr. |
| 4,994,069 A | 2/1991 | Ritchart et al. |
| 4,994,071 A | 2/1991 | MacGregor |
| 5,035,705 A | 7/1991 | Burns |
| 5,108,407 A | 4/1992 | Geremia et al. |
| 5,122,136 A | 6/1992 | Guglielmi et al. |
| 5,135,486 A | 8/1992 | Eberle et al. |
| 5,137,514 A | 8/1992 | Ryan |
| 5,167,624 A | 12/1992 | Butler et al. |
| 5,168,757 A | 12/1992 | Rabenau et al. |
| 5,201,754 A | 4/1993 | Crittenden et al. |

(List continued on next page.)

FOREIGN PATENT DOCUMENTS

| EP | 0 717 969 | 6/1996 |
| EP | 0 739 607 | 10/1996 |
| WO | WO 96/02100 | 1/1996 |
| WO | WO 98/02100 | 1/1998 |

OTHER PUBLICATIONS

Brochure entitled, "Guglielmi Detachable Coils," by Boston Scientific Label of IDC–18 Interlocking Detachable Coil by Target Therapeutics, Inc.
Brochure entitled, "Detachable Coil System, " by Cook.
Brochure entitled, "Basix25™ Inflation Device," by Merit Medical Systems, Inc.
Brochure entitled, "MonarchAP® Inflation Device," by Merit Medical System, Inc. Label of B. Braun Inflation Device Kit by B. Braun Medical Inc.
U.S. Patent application Ser. No. 09/382,967, filed Aug. 25, 1999, entitled "Hydraulic Stent Deployment System".
U.S. Patent Application Ser. No. 09/515,944, filed Feb. 29, 2000, entitled, "Embolic Coil Hydraulic Deployment System With Purge Mechanism".

*Primary Examiner*—Kevin Truong
(74) *Attorney, Agent, or Firm*—Henry W. Collins

(57) ABSTRACT

A medical device for placing a very small embolic coil at a preselected location within a vessel comprising a positioning catheter having a distal tip for retaining a headpiece with an attached embolic coil such that when the catheter is pressurized with a fluid the distal tip of the catheter expands outwardly to release the headpiece and coil at the preselected position.

14 Claims, 2 Drawing Sheets

U.S. PATENT DOCUMENTS

| | | |
|---|---|---|
| 5,217,484 A | 6/1993 | Marks |
| 5,234,437 A | 8/1993 | Sepetka |
| 5,250,071 A | 10/1993 | Palermo |
| 5,261,916 A | 11/1993 | Engelson |
| 5,263,964 A | 11/1993 | Purdy |
| 5,304,195 A | 4/1994 | Twyford, Jr. et al. |
| 5,312,415 A | 5/1994 | Palermo |
| 5,334,210 A | 8/1994 | Gianturco |
| 5,336,183 A | 8/1994 | Greelis et al. |
| 5,342,304 A | 8/1994 | Tacklind et al. |
| 5,350,397 A | 9/1994 | Palermo et al. |
| 5,382,259 A | 1/1995 | Phelps et al. |
| 5,403,292 A | 4/1995 | Ju |
| 5,443,478 A | 8/1995 | Purdy |
| 5,470,317 A | 11/1995 | Cananzey et al. |
| 5,534,007 A | 7/1996 | St. German et al. |
| 5,551,954 A | 9/1996 | Buscemi et al. |
| 5,578,074 A | 11/1996 | Mirigian |
| 5,582,619 A | 12/1996 | Ken |
| 5,601,600 A | 2/1997 | Ton |
| 5,609,608 A | 3/1997 | Bennett et al. |
| 5,647,847 A | 7/1997 | Lafontaine et al. |
| 5,690,667 A | 11/1997 | Gia |
| 5,728,065 A | 3/1998 | Follmer et al. |
| 5,772,668 A | 6/1998 | Summers et al. |
| 5,817,057 A | 10/1998 | Berenstein et al. |
| 5,853,418 A | 12/1998 | Ken et al. |
| 5,925,059 A * | 7/1999 | Palermo et al. ............. 606/191 |
| 5,928,226 A * | 7/1999 | Guglielmi et al. .......... 606/108 |
| 6,068,644 A | 5/2000 | Lulo et al. |
| 6,117,142 A | 9/2000 | Goodson et al. |

* cited by examiner

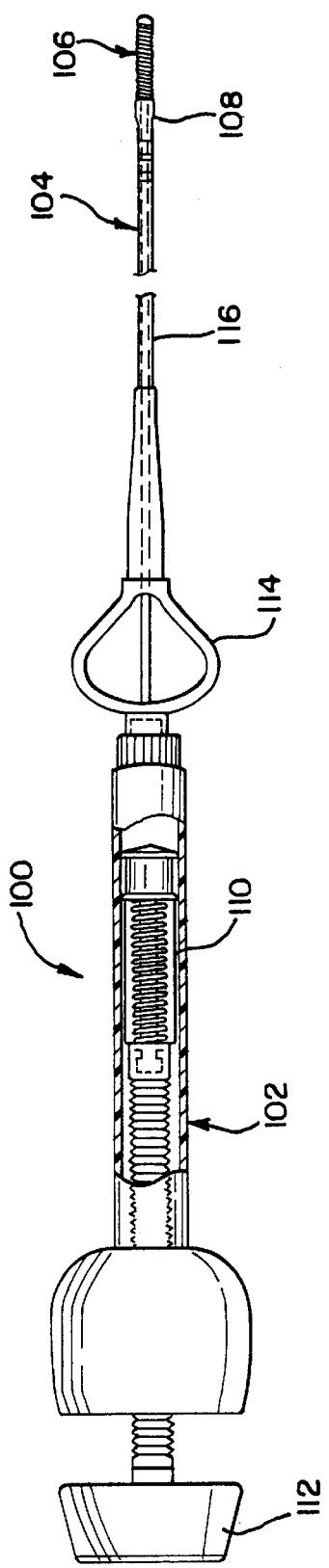

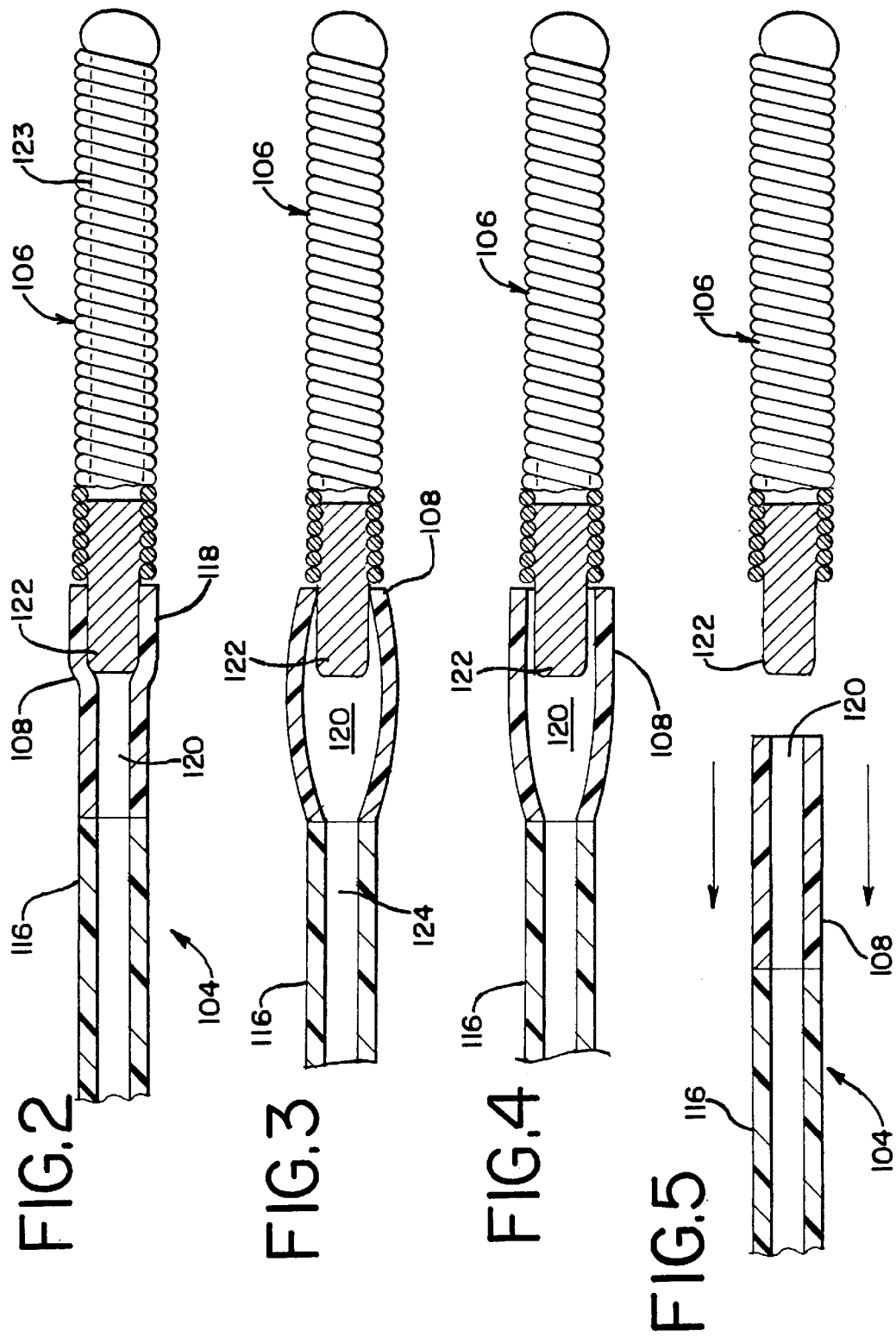

SMALL DIAMETER EMBOLIC COIL HYDRAULIC DEPLOYMENT SYSTEM

This application is a continuation of U.S. application Ser. No. 09/177,848, filed Oct. 22, 1998 now U.S. Pat. No. 6,113,622.

BACKGROUND OF THE INVENTION

1. Field of the Invention

The present invention relates to a medical device for placing an embolic coil at a preselected location within a vessel of the human body, and more particularly, relates to a very small diameter catheter having a distal tip for retaining an embolic coil in order to transport the coil to a preselected position within the vessel and a control mechanism for releasing the embolic coil at the preselected position. This device is particularly suited to transport an embolic coil through the tortuous vasculature of the human brain.

2. Description of the Prior Art

For many years flexible catheters have been used to place various devices within the vessels of the human body. Such devices include dilatation balloons, radiopaque fluids, liquid medications and various types of occlusion devices such as balloons and embolic coils. Examples of such catheter devices are disclosed in U.S. Pat. No. 5,108,407, entitled "Method And Apparatus For Placement Of An Embolic Coil"; U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose devices for delivering embolic coils to preselected positions within vessels of the human body in order to treat aneurysms, or alternatively, to occlude blood vessels at a particular location.

Coils which are placed in vessels may take the form of helically wound coils, or alternatively, may be random wound coils, coils wound within coils or many other such coil configurations. Examples of various coil configurations are disclosed in U.S. Pat. No. 5,334,210, entitled, "Vascular Occlusion Assembly; U.S. Pat. No. 5,382,259, entitled, "Vasoocclusion Coil With Attached Tubular Woven Or Braided Fibrous Covering." Embolic coils are generally formed of a radiopaque metallic materials, such as platinum, gold, tungsten or alloys of these metals. Often times several coils are placed at a given location in order to occlude the flow of blood through the vessel by promoting thrombus formation at the particular location.

In the past, embolic coils have been placed within the distal end of the catheter. When the distal end of the catheter is properly positioned the coil may then be pushed out of the end of the catheter with a guidewire in order to release the coil at the desired location. This procedure of placement of the embolic coil is conducted under fluoroscopic visualization such that the movement of the coil through the vasculature of the body may be monitored and the coil may be placed in the desired location. With these placements systems there is very little control over the exact placement of the coil since the coil may be ejected to a position some distance beyond the end of the catheter. As is apparent, with these latter systems, when the coil has been released from the catheter it is difficult, if not impossible, to retrieve the coil or to reposition the coil.

Numerous procedures have been developed to enable more accurate positioning of coils within a vessel. Still another such procedure involves the use of a glue or solder for attaching the embolic coil to a guidewire, which is in turn, placed within a flexible catheter for positioning the coil within the vessel at a preselected position. Once the coil is at the desired position, the coil is held in position by the catheter and the guidewire is pulled from the proximal end of the catheter to thereby cause the coil to become detached from the guidewire and released from the catheter. Such a coil positioning system is disclosed in U.S. Pat. No. 5,263,964, entitled, "Coaxial Traction Detachment Apparatus And Method."

Another coil positioning system utilizes a catheter having a socket at the distal end of the catheter for retaining a ball which is bonded to the proximal end of the coil. The ball, which is larger in diameter than the outside diameter of the coil, is placed in a socket within the lumen at the distal end of the catheter and the catheter is then moved into a vessel in order to place the coil at a desired position. Once the position is reached, a pusher wire with a piston at the end thereof is pushed distally from the proximal end of the catheter to thereby push the ball out of the socket in order to thereby release the coil at the desired position. Such a system is disclosed in U.S. Pat. No. 5,350,397, entitled, "Axially Detachable Embolic Coil Assembly." One problem with this type of coil placement system which utilizes a pusher wire which extends through the entire length of the catheter and which is sufficiently stiff to push an attachment ball out of engagement with the socket at the distal end of the catheter is that the pusher wire inherently causes the catheter to be too stiff with the result that it is very difficult to guide the catheter through the vasculature of the body.

Another method for placing an embolic coil is that of utilizing a heat releasable adhesive bond for retaining the coil at the distal end of the catheter. One such system uses laser energy which is transmitted through a fiber optic cable in order to apply heat to the adhesive bond in order to release the coil from the end of the catheter. Such a method is disclosed in U.S. Pat. No. 5,108,407, entitled, "Method And Apparatus For Placement Of An Embolic Coil." Such a system also suffers from the problem of having a separate fiber optic element which extends throughout the length of the catheter with resulting stiffness to the catheter.

Still another coil deployment system incorporates a catheter having a lumen throughout the length of the catheter and a distal tip for retaining the coil for positioning the coil at a preselected site. The distal tip of the catheter is formed of a material which exhibits the characteristic that when the lumen of the catheter is pressurized the distal tip radially expands to release the coil at the preselected site. Such a deployment system is disclosed in the parent patent application, U.S. patent No. application Ser. No. 09/177,848, filed on Oct. 22, 1998, and entitled, "Embolic Coil Hydraulic Deployment System," assigned to the assignee of the present patent application.

SUMMARY OF THE INVENTION

The present invention is directed toward a very small diameter vascular occlusive coil deployment system for use in placing an embolic coil at a preselected site within a vessel which includes a small diameter, flexible catheter having a distal tip for retaining the coil so that the coil may be moved to the preselected site within the vessel. The catheter has a lumen which extends therethrough the length of the catheter and also includes a distal end which is formed of a material having a durometer such that when a fluid pressure of about 300 pounds per square inch (psi) is applied to the interior of the catheter, the walls of the distal tip expand outwardly, or radially, to thereby increase the lumen of the distal tip of the catheter. The embolic coil is disposed upon and bonded to a cylindrical headpiece which has a diameter approximately equal to the diameter of the lumen of the catheter. The headpiece extends outwardly from the proximal end of the coil and this portion of the headpiece is disposed within and retained by the lumen at the distal tip of the catheter. A hydraulic injector, such as a syringe, is coupled to the proximal end of the catheter for applying a fluid pressure to the lumen of the catheter. When the coil is placed at a desired position within a vessel, fluid pressure is applied to the lumen of the catheter by the hydraulic injector to thereby cause the walls of the distal tip to expand outwardly, or radially, to release the headpiece which carries with it the coil. Most importantly, the diameter of the headpiece is approximately equal to or slightly larger, than the diameter of the lumen of the catheter so that when the headpiece 122 is inserted into the distal section of the catheter, the outside diameter of the attached coil 106 is approximately equal to the outside diameter of the catheter. This construction results in a deployment system having an overall outside diameter approximately equal to that of the catheter.

In accordance with another aspect of the present invention, the flexible catheter is comprised of a proximal section and a relatively short distal section. The proximal section is formed of a material which is sufficiently flexible to be passed through the vasculature of the human body and is of a durometer which essentially resists outward expansion when a fluid pressure on the order of about 300 psi is applied to the interior of the catheter. The distal section of the catheter is formed of a material which is also sufficiently flexible to be passed through the vasculature of the body, yet is of a durometer which is significantly lower than the durometer of the proximal section and exhibits the property of expanding outwardly, or radially, when such a fluid pressure is applied to the interior of the catheter to thereby permit the release of the headpiece to thereby release the embolic coil.

In accordance with still another aspect of the present invention, the distal section of the catheter has a durometer in a range of between about 25D and 55D.

In still another aspect of the present invention, the embolic coil is comprised of a helical coil having a proximal end, a distal end, and a lumen extending therethrough. A headpiece is partially disposed within the lumen of the proximal end of the coil and the other portion of the headpiece is placed in fluid-tight engagement with the lumen of the catheter.

In another aspect of the present invention, the hydraulic injector for applying a fluid pressure to the interior of the catheter takes the form of a syringe which is coupled to the proximal end of the catheter for, upon movement of the piston, creating a fluid pressure which is applied to the interior of the catheter to thereby cause the release of the embolic coil.

In accordance with another aspect of the present invention, the embolic coil may take the form of other types of implantable devices, such as a vascular filter.

These aspects of the invention and the advantages thereof will be more clearly understood from the following description and drawings of a preferred embodiment of the present invention:

BRIEF DESCRIPTION OF THE DRAWINGS

FIG. 1 is an enlarged, partial sectional view of the hydraulic vascular occlusive coil deployment system of the present invention;

FIG. 2 is an enlarged partially sectional view showing the distal end of the coil deployment system prior to deployment of the coil;

FIGS. 3 and 4 illustrate the sequential steps in the radial expansion of the distal tip of the coil deployment system as the embolic coil is released; and, FIG. 5 illustrates the distal tip of the coil deployment system after release of the embolic coil.

DESCRIPTION OF A PREFERRED EMBODIMENT

FIG. 1 generally illustrates the vascular occlusive coil deployment system 100 which is comprised of a hydraulic injector or syringe 102, coupled to the proximal end of a catheter 104. An embolic coil 106 includes a proximal headpiece 122 which is disposed within the lumen of the distal end 108 of the catheter. The headpiece 122 is tightly held within the lumen of the distal section 108 of the catheter 104 until the deployment system is activated for release of the coil. As may be seen, the syringe 102 includes a threaded piston 110 which is controlled by a handle 112 for infusing fluid into the interior of the catheter 104. Also as illustrated, the catheter 104 includes a winged hub 114 which aides in the insertion of the catheter into the vascular system of the body.

FIG. 2 illustrates in more detail the distal end of the catheter 104. The catheter 104 includes a proximal section 116 and the distal section 108. The embolic coil 106 is tightly wrapped and bonded to the distal portion of a cylindrical headpiece 122. The proximal portion of the headpiece 122 is disposed within the distal section 108 of the catheter and is tightly held within the lumen 120 of this distal section 108 prior to release of the headpiece 122 and attached coil 106. As may be appreciated, FIG. 2 illustrates the vascular occlusive coil deployment system prior to activation of the piston of the syringe and prior to release of the coil.

The embolic coil 106 may take various forms and configurations and may even take the form of a randomly wound coil, however, with the helical wound coil as illustrated in FIG. 2, the coil is provided with a headpiece 122 having a proximal portion which is disposed in a lumen 120 which lumen extends throughout the length of the coil 106. The headpiece 122 serves to retain the coil 106 and also to prevent the flow of fluid through the lumen of the coil 106. When the headpiece 122 is placed in fluid-tight engagement with the lumen 120 the headpiece serves to provide a fluid-tight seal at the distal end of the catheter 104. Adjacent turns of the coil 106 at the proximal end 118 of the coil are preferably continuously welded together and are in turn welded to the headpiece 122 to provide a generally unitary structure. Most importantly, the diameter of the headpiece is approximately equal to or slightly larger, than the diameter of the lumen of the catheter so that when the headpiece 122 is inserted into the distal section of the catheter, the outside diameter of the attached coil 106 is approximately equal to the outside diameter of the catheter. This construction results in a deployment system having an overall outside diameter approximately equal to that of the catheter.

Preferably, the proximal section 116 and the distal section 108 of the catheter 104 are formed of materials having different durometers. The proximal section 116 is preferably formed of Pebax material having a durometer in a range of about 62D to 75D. The proximal section is sufficiently flexible to transverse the vasculature of the human body, but is sufficiently rigid such that when a fluid pressure of approximately 300 psi is applied to the interior of this section of the catheter there is very little, if any, radial expansion of the walls of this section. On the other hand, the distal section 108 of the catheter is preferably formed of polymer material with a relatively low durometer which, exhibits the characteristic that when a fluid pressure of approximately 300 psi is applied to the interior of the catheter the walls of the distal section 108 expand radially, somewhat similar to the action of a balloon inflating, to thereby release the proximal end 118 of the coil 106. As may be appreciated, there are numerous materials which could be used to fabricate the proximal section 116 and distal section 108 of the catheter 104, however, the distal section 108 is preferably formed from a block copolymer such as Pebax having a durometer of between 25D and 55D with a durometer of 40D being the preferred durometer.

FIGS. 3 and 4 generally illustrate the coil release mechanism in action for the vascular occlusive catheter deployment system. More particularly, as shown in FIG. 3, when a hydraulic pressure is applied to the interior 124 of the catheter 104 the relatively low durometer distal section 108 of the catheter begins to expand radially, much as a balloon expands during the process of inflation. As the distal section 108 continues to expand radially there comes a point as illustrated in FIG. 4 in which the headpiece 122 and attached coil 106 becomes disengaged from the lumen of the distal section 108 and the coil is then released from the catheter and is deployed within the vessel.

As illustrated in FIG. 5, when the headpiece 122 and the coil 106 have been released from the catheter 104, the catheter may then be withdrawn leaving the coil positioned at the desired site.

With the vascular occlusive coil deployment system of the present invention it is possible to place an embolic coil very precisely at a desired location within a vessel. Once the coil has been placed in that location by use of the catheter, the catheter may be activated by applying a hydraulic pressure to the interior of the catheter to thereby cause the catheter to release the coil and deposit the coil very accurately at the desired location.

As is apparent, there are numerous modifications of the preferred embodiment described above which will be readily apparent to one skilled in the art, such as many variations and modifications of the coil including numerous coil winding configurations, or alternatively other types of implant devices, such as a vascular filter. Also, there are obviously variations of the syringe arrangement for applying a fluid pressure to the interior of the catheter, including many other fluid pressure generating systems for increasing the pressure within the interior of a catheter in order to cause the distal section of the catheter to expand. These modifications would be apparent to those having ordinary skill in the art to which this invention relates and are intended to be within the scope of the claims which follow.

That which is claimed is:

1. A small diameter vasocclusive coil deployment system for use in placing a coil at a preselected site within a vessel comprising:

an elongated flexible catheter having a lumen extending therethrough so as to define an outer wall and having a proximal sect ion and a distal section, said distal section of the catheter being formed of a material having a durometer which exhibits the characteristic that when a fluid pressure is applied to the lumen of the catheter the outer wall of the distal section of the catheter is caused to expand outwardly;

an embolic coil assembly comprised of a helically wound flexible coil having proximal and distal ends and a cylindrical headpiece having proximal and distal sections, the distal section of the headpiece is disposed within the proximal end of the helically wound coil and the proximal section of the headpiece extends outwardly beyond the proximal end of the helically wound coil, said proximal section of the cylindrical headpiece having a diameter approximately equal to the diameter of the lumen of the catheter and said proximal section of said cylindrical headpiece being disposed in fluid-tight engagement within the lumen of the distal section of the catheter; and, a syringe coupled to the proximal section of the catheter for applying a fluid pressure to the interior of the catheter to thereby cause the distal section of the catheter to expand outwardly to thereby release the cylindrical headpiece to thereby deploy the embolic coil assembly.

2. A vasoocclusive coil deployment system as defined in claim 1, wherein said proximal section of said catheter is formed of a material which is sufficiently flexible to be passed through the vasculature of the body and is formed of a material which exhibits the characteristic of having substantially no radial expansion when a fluid pressure of about 300 psi is applied to the lumen of the proximal section of the catheter, the distal section is formed of a material which is also sufficiently flexible to be passed through the vasculature of the body and is of a durometer which is substantially lower than the durometer of the proximal section.

3. A vasoocclusive coil deployment system as defined in claim 1, wherein the helically wound coil has an outside diameter which is approximately equal to an outside diameter of the catheter to thereby provide a coil deployment system of a uniform outside diameter.

4. A vasoocclusive coil deployment system as defined in claim 3, wherein the distal section of the catheter is formed of a polymer having a durometer in a range of between 25D and 55D.

5. A vasoocclusive coil deployment system as defined in claim 3, wherein the distal section of the catheter is formed of a polymer having a durometer of about 45D.

6. A small diameter vasoocclusive coil deployment system for use in placing a coil at a preselected site within a vessel comprising:

an elongated flexible catheter having a lumen extending therethrough so as to define an outer wall and having a proximal section and a distal section, said distal section of the catheter being formed of a material having a durometer which exhibits the characteristic that when a fluid pressure is applied to the lumen of the catheter the outer wall of the distal section of the catheter is caused to expand outwardly;

an embolic coil assembly comprised of a flexible coil having proximal and distal ends and a cylindrical headpiece having proximal and distal sections, the distal section of the headpiece is disposed within the proximal end of the coil and the proximal section of the headpiece extends outwardly beyond the proximal end of the coil, said proximal section of the cylindrical headpiece having a diameter approximately equal to the diameter of the lumen of the catheter and said proximal section of said cylindrical headpiece being disposed in fluid-tight engagement within the lumen of the distal section of the catheter; and, a connector coupled to the proximal section of the catheter and adapted for coupling a source of fluid pressure to the interior of the catheter to thereby cause the distal section of the catheter to expand outwardly to thereby release the cylindrical headpiece to thereby deploy the embolic coil assembly.

7. A vasoocclusive coil deployment system as defined in claim 6, wherein said proximal section of said catheter is formed of a material which is sufficiently flexible to be passed through the vasculature of the body and is formed of a material which exhibits the characteristic of having substantially no radial expansion when a fluid pressure of about 300 psi is applied to the lumen of the proximal section of the catheter, the distal section is formed of a material which is also sufficiently flexible to be passed through the vasculature of the body and is of a durometer which is substantially lower than the durometer of the proximal section.

8. A vasoocclusive coil deployment system as defined in claim 6, wherein the coil has an outside diameter which is approximately equal to an outside diameter of the catheter to thereby provide a coil deployment system of a uniform outside diameter.

9. A small diameter vasocclusive medical device deployment system for use in placing a medical device at a preselected site within a vessel comprising:

an elongated flexible catheter having a lumen extending therethrough so as to define an outer wall and having a proximal section and a distal section, said distal section of the catheter being formed of a material having a durometer which exhibits the characteristic that when a fluid pressure is applied to the interior of the catheter the walls of the distal section of the catheter expand outwardly;

a medical device assembly comprised of a medical device having proximal and distal ends and a cylindrical headpiece having proximal and distal sections, the distal section of the headpiece is coupled to the proximal end of the medical device and the proximal section of the headpiece extends outwardly beyond the proximal end of the medical device, said proximal section of the cylindrical headpiece having a diameter approximately equal to the diameter of the lumen of the catheter and said proximal section of said cylindrical headpiece bring disposed in fluid-tight engagement with the lumen of the distal section of the catheter; and, a connector coupled to the proximal section of the catheter and adapted for coupling a source of fluid pressure to the interior of the catheter to thereby cause the distal section of the catheter to expand outwardly to thereby release the cylindrical headpiece with the medical, device.

10. A vasoocclusive medical device deployment system as defined in claim 9, wherein said proximal section of said catheter is formed of a material which is sufficiently flexible to be passed through the vasculature of the body and is formed of a material which exhibits the characteristic of having substantially no radial expansion when a fluid pressure of about 300 psi is applied to the lumen of proximal section of the catheter, the distal section is formed of a material which is also sufficiently flexible to be passed through the vasculature of the body and is of a durometer which is substantially lower than the durometer of the proximal section.

11. A vasoocclusive medical device deployment system as defined in claim 9, wherein the Medical device has an outside diameter which is approximately equal to the outside diameter of the catheter to thereby provide a medical device deployment system of a uniform outside diameter.

12. A small diameter vasocclusive coil deployment system for use in placing a coil at a preselected site within a vessel comprising:

an elongated flexible catheter having a lumen extending therethrough so as to define an outer wall and having a proximal section and a distal section, said distal section of the catheter being formed of a material having a durometer which exhibits the characteristic that when a fluid pressure generating device is applied to the lumen of the catheter the outer wall of the distal section of the catheter is caused to expand outwardly;

an embolic coil assembly comprised of a helically wound flexible coil having proximal and distal ends and a cylindrical headpiece having proximal and distal sections, the distal section of the headpiece is disposed within the proximal end of the coil and the proximal section of the headpiece extends outwardly beyond the proximal end of the coil, said proximal section of the cylindrical headpiece having a diameter approximately equal to the diameter of the lumen of the catheter and said proximal section of said cylindrical headpiece being disposed in fluid-tight engagement with the lumen of the distal section of the catheter; and, a source of fluid pressure coupled to the proximal section of the catheter for applying a fluid pressure to the interior of the catheter to thereby cause the distal section of the catheter to expand outwardly to thereby release the cylindrical headpiece to thereby deploy the embolic coil assembly.

13. A vasoocclusive coil deployment system as defined in claim 12, wherein said proximal section of said catheter is formed of a material which is sufficiently flexible to be passed through the vasculature of the body and is formed of a material which exhibits the characteristic of having substantially no radial expansion when a fluid pressure of about 300 psi is applied to the lumen of the proximal section of the catheter, the distal section is formed of a material which is also sufficiently flexible to be passed through the vasculature of the body and is of a durometer which is substantially lower than the durometer of the proximal section.

14. A vasoocclusive coil deployment system as defined in claim 12, wherein the helically wound coil has an outside diameter which is approximately equal to an outside diameter of the catheter to thereby provide a coil deployment system of a uniform outside diameter.

* * * * *